United States Patent
Choi et al.

(10) Patent No.: US 12,217,594 B2
(45) Date of Patent: Feb. 4, 2025

(54) GAS DETECTION DEVICE

(71) Applicant: POSCO Co., Ltd, Pohang-si (KR)

(72) Inventors: Cheol-hee Choi, Pohang-si (KR); Kisoo Kim, Pohang-si (KR); Dukman Lee, Pohang-si (KR)

(73) Assignee: POSCO CO., LTD, Pohang-si (KR)

( * ) Notice: Subject to any disclaimer, the term of this patent is extended or adjusted under 35 U.S.C. 154(b) by 0 days.

(21) Appl. No.: 18/268,171

(22) PCT Filed: Sep. 1, 2021

(86) PCT No.: PCT/KR2021/011770
§ 371 (c)(1),
(2) Date: Jun. 16, 2023

(87) PCT Pub. No.: WO2022/131484
PCT Pub. Date: Jun. 23, 2022

(65) Prior Publication Data
US 2024/0296731 A1    Sep. 5, 2024

(30) Foreign Application Priority Data
Dec. 18, 2020   (KR) .......................... 10-2020-0178275

(51) Int. Cl.
*G08B 21/14*   (2006.01)
*G01N 1/22*   (2006.01)
(Continued)

(52) U.S. Cl.
CPC .......... *G08B 21/14* (2013.01); *G01N 1/2205* (2013.01); *G01N 1/2273* (2013.01); *G08B 5/223* (2013.01);
(Continued)

(58) Field of Classification Search
CPC .......... G08B 21/14; G08B 5/223; G08B 7/06; G01N 1/2205; G01N 1/2273;
(Continued)

(56) References Cited

U.S. PATENT DOCUMENTS 8,537,020 B2    9/2013   Thorson
2008/0173817 A1   7/2008   Goldstein et al.
(Continued)

FOREIGN PATENT DOCUMENTS

CN    106052736 A    10/2016
JP    2620787 B2    6/1997
(Continued)

OTHER PUBLICATIONS

Notice of Allowance issued in corresponding Korean Patent Application No. 10-2020-0178275 dated Jun. 19, 2023, with English translation.
(Continued)

*Primary Examiner* — An T Nguyen
(74) *Attorney, Agent, or Firm* — Morgan, Lewis & Bockius LLP

(57) ABSTRACT

A gas detection device is disclosed. A gas detection device according to an embodiment of the present invention includes a case in which a plurality of grooves are formed in a circumferential surface, an inlet which is coupled to a first groove among the grooves and through which air is introduced into the case, a power button which is coupled to a second groove among the grooves and turns a power source on or off, a gas detector which is provided in the case and detects a gas contained in the introduced air, a light unit which is coupled to a third groove among the grooves and informs a state in which the power source is turned on or off and whether the gas is detected, a battery which supplies power, a beep generator which generates a beep when a gas (Continued)

detection signal is received from the gas detector, and a power switch operated by the power button to turn on or off so as to supply the power from the battery, wherein one or more of the inlet, the power button, and the light unit are coupled to the grooves in a recessed form, the battery, the beep generator, and the power switch are provided inside the case, and the case is formed in a small spherical shape which is carried in a palm of an operator and moved by the operator.

5 Claims, 2 Drawing Sheets

(51) Int. Cl.
    *G08B 5/22*         (2006.01)
    *G08B 7/06*         (2006.01)

(52) U.S. Cl.
    CPC ....... *G08B 7/06* (2013.01); *G01N 2001/2276* (2013.01)

(58) Field of Classification Search
    CPC ....... G01N 2001/2276; G01N 33/0009; G01N 27/26; G01N 2015/0046; G01N 2027/222
    See application file for complete search history.

(56) References Cited

U.S. PATENT DOCUMENTS

| | | |
|---|---|---|
| 2010/0156647 A1 | 6/2010 | Thorson |
| 2017/0131253 A1 | 5/2017 | Gutierrez Martinez |
| 2018/0321209 A1 | 11/2018 | Gutierrez Martinez |
| 2019/0265082 A1 | 8/2019 | Zafar et al. |

FOREIGN PATENT DOCUMENTS

| | | | |
|---|---|---|---|
| JP | H11-160277 | A | 6/1999 |
| KR | 10-2011-0038213 | A | 4/2011 |
| KR | 20-0477918 | Y1 | 8/2015 |
| KR | 10-1588415 | B1 | 1/2016 |
| KR | 10-2017-0027446 | A | 3/2017 |
| KR | 10-2018-0079788 | A | 7/2018 |
| KR | 10-1947598 | B1 | 4/2019 |

OTHER PUBLICATIONS

Japanese Office Action dated May 7, 2024 issued in Japanese Patent Application No. 2023-537420 (with English translation).
International Search Report dated Nov. 29, 2021 issued in International Patent Application No. PCT/KR2021/011770 (with English translation).
The Extended European Search Report dated Nov. 11, 2024 issued in European Patent Application No. 21906789.9.

GAS DETECTION DEVICE

CROSS-REFERENCE OF RELATED APPLICATIONS

This application is the U.S. National Phase under 35 U.S.C. § 371 of International Patent Application No. PCT/KR2021/011770, filed on Sep. 1, 2021 which claims priority to and the benefit of Korean Application Nos. 10-2020-0178275 filed on Dec. 18, 2020, the entire contents of which are incorporated herein by reference.

TECHNICAL FIELD

The present invention relates to a gas detection device.

BACKGROUND ART

When harmful gases exist in closed spaces, mortality accidents may occur. To prevent this, various gas detection devices have been conventionally used.

However, since an operator has to carry a gas detection device and measure harmful gases, an accident risk still exists, and it is inconvenient to carry the gas detection device due to the weight of the gas detection device.

In addition, since it is difficult to detect harmful gases in a deep and cramped place which is difficult for the operator to approach and additional means are required, installation and operation costs can be increased.

Technical Problem

An embodiment of the present invention is directed to providing a gas detection device which is easy to carry and capable of quickly detecting gases existing in any place by only throwing the gas detection device.

Technical Solution

One aspect of the present invention provides a gas detection device including a case in which a plurality of grooves are formed in a circumferential surface, an inlet which is coupled to a first groove among the grooves and through which air is introduced into the case, a power button which is coupled to a second groove among the grooves and turns a power source on or off, a gas detector which is provided in the case and detects a gas contained in the introduced air, a light unit which is coupled to a third groove among the grooves and informs a state in which the power source is turned on or off and whether the gas is detected, a battery which supplies power, a beep generator which generates a beep when a gas detection signal is received from the gas detector, and a power switch operated by the power button to turn on or off so as to supply the power from the battery, wherein one or more of the inlet, the power button, and the light unit are coupled to the grooves in a recessed form, the battery, the beep generator, and the power switch are provided inside the case, and the case is formed in a small spherical shape which is carried in a palm of an operator and moved by the operator.

The case may have a shape in which an upper case having a hemispherical shape and a lower case having a hemispherical shape are coupled, and an outer cover of the case may be formed of an elastic material and formed in a shape in which hexagonal shapes are consecutively arranged.

The inlet may include a filter exposed to the outside and a guide member in which a hole is formed so that air passing through the filter flows to the gas detector.

The gas detection device may further include a support frame provided above the battery, wherein the battery, the support frame, and the gas detector coupled to an upper portion of the support frame, the beep generator, and the power switch may be sequentially disposed in the case from a lower side so that a center of gravity is present at a lower portion.

The gas detection device may further include a transmitter through which information on the detected gas is transmitted to a smartphone.

Advantageous Effects

A gas detection device according to embodiments of the present invention is easy to carry and can quickly detect a gas existing in any place by only throwing the gas detection device.

In addition, the presence of a gas can be immediately informed visually and audibly.

MODES OF THE INVENTION

Figure 1:
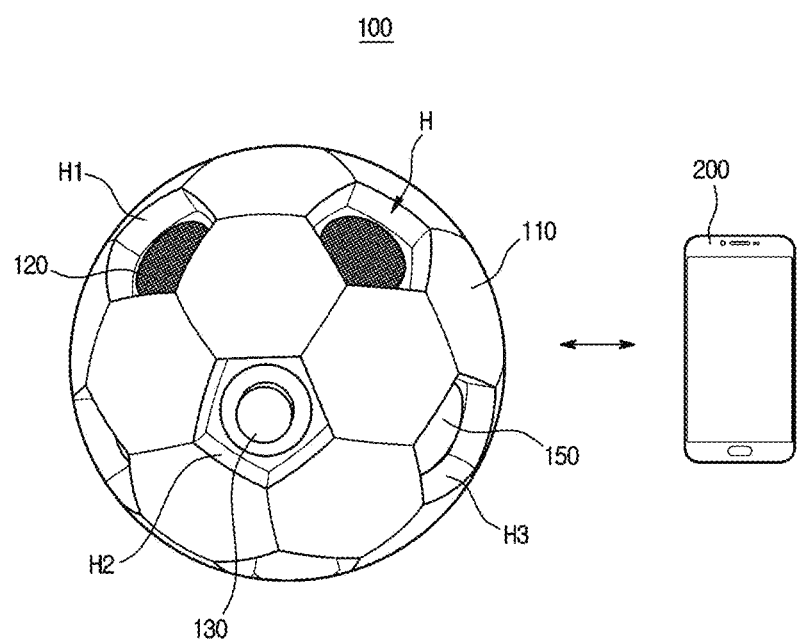
FIG. 1 is a view illustrating a gas detection device according to an embodiment of the present invention.

Hereinafter, embodiments of the present disclosure will be described in detail with reference to the accompanying drawings. The embodiments, which will be described below, are examples which provide the concept of the present disclosure to those skilled in the art. The present disclosure is not limited to the embodiments, and may be implemented in different forms. Parts irrelevant to description are omitted in the drawings in order to clearly describe the present disclosure, and widths, lengths, and thicknesses of components in the drawings may be exaggerated for convenience of description. In this specification, like reference characters denote like components.

Figure 2:
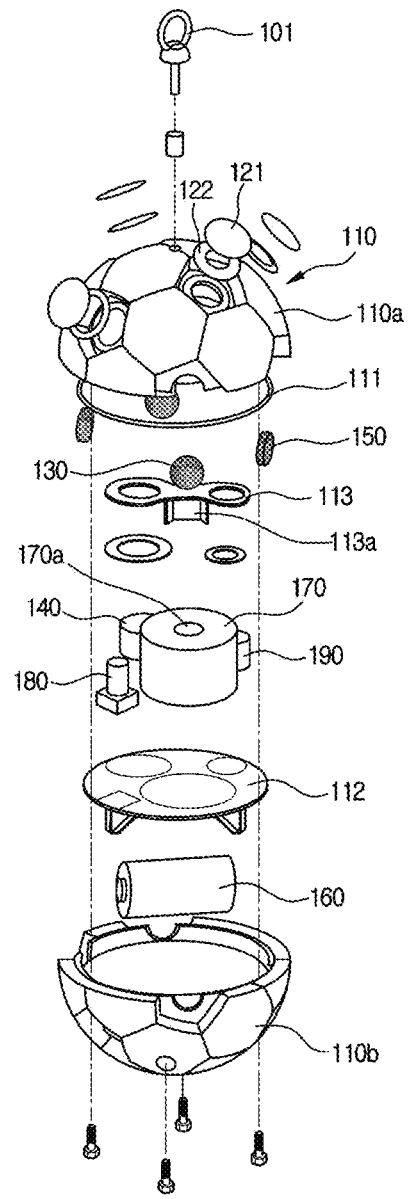
FIG. 2 is an exploded view illustrating the gas detection device of FIG. 1.

FIG. 1 is a view illustrating a gas detection device according to an embodiment of the present invention, and FIG. 2 is an exploded view illustrating the gas detection device of FIG. 1.

Referring to FIGS. 1 and 2, a gas detection device 100 includes a case 110 in which a plurality of grooves H are formed in a circumferential surface of the case 110, an inlet 120 which is coupled to a first groove H1 among the grooves H and through which air is introduced into the case 110, a power button 130 which is coupled to a second groove H2 among the grooves H and turns a power source on or off, a gas detector 140 which is provided in the case 110 and detects a gas contained in the air introduced through the inlet 120, and a light unit 150 which is coupled to a third groove H3 among the grooves H and informs an on or off state of the power source and whether a gas is detected.

In addition, the gas detection device 100 may include a battery 160 which supplies power, a beep generator 170 which generates a beep when a gas is detected, and a power switch 180 which is turned on or off by the power button 130.

In this case, one or more of the inlet 120, the power button 130, and the light unit 150 are coupled to the grooves H in a recessed form.

In addition, the case 110 may be formed in a portable spherical shape, and an outer cover of the case 110 may be formed of an elastic material. The case 110 may be provided in the spherical shape in which convex hexagonal covers are connected. Accordingly, the gas detection device 100 can be easily carried and thrown into a desired space.

The gas detection device 100 may be manufactured in the small spherical shape which may be easily carried in a palm of an operator and moved by the operator, and a ring 101 may be provided at an upper end of the gas detection device 100 to be bound to an operator's clothes so that convenience of portability and movement can be improved.

In addition, a strap (not shown) may be connected to the ring 101, the gas detection device 100 may be thrown into a place in which gas detection is required while the operator is holding the strap, and the gas detection device 100 may be easily collected by pulling the strap. For example, a fishing line connected to a fishing rod may be connected to the ring 101, the gas detection device 100 may be thrown into a place in which gas detection is required, and then the gas detection device 100 may be collected by winding the fishing line.

The gas detection device 100 may be thrown into a closed space or the like and detect gas or analyze gas components, and provide information to one or more external devices through data communication.

Hereinafter, each component of the gas detection device 100 will be described in detail.

In the circumferential surface of the case 110, the plurality of grooves H are formed, and one or more of the inlet 120, power button 130, and the light unit 150 may be coupled to the grooves H in a recessed form. Accordingly, when the gas detection device 100 is thrown, the inlet 120, the power button 130, and the light unit 150 can be prevented from being damaged by impact. The inlet 120, the power button 130, and the light unit 150 may be coupled to the first groove H1, the second groove H2, and the third groove H3, respectively, and each of the grooves H1 to H3 may be formed in a hexagonal shape. The first groove H1 in which the inlet 120 is provided may be provided as two or more first grooves H1 at set positions, and one second groove H2 in which the power button 130 is provided may be formed. In addition, the third groove H3, in which the light unit 150 is provided, may be provided as two or more third grooves H3 at set positions.

The case 110 may have a shape in which an upper case 110a having a hemispherical shape is coupled to a lower case 110b having a hemispherical shape. When the upper case 110a and the lower case 110b are coupled, an O-ring 111 for sealing may be used therebetween.

The case 110 may have the spherical shape formed by the upper case 110a and the lower case 110b that are coupled, and the outer cover of the case 110 may be formed of the elastic material including rubber. Accordingly, an impact, when the gas detection device 100 is thrown, can be reduced, and an operation of the gas detection device 100 can be performed normally.

In addition, the outer cover of the case 110 may have a shape in which hexagonal shapes are consecutively arranged, and in another example, may be formed in a shape in which hexagonal shapes and pentagonal shapes are mixed. Accordingly, the gas detection device 100 can provide familiarity to the operator and reduce slippage, and thus the operator can easily grip the gas detection device 100 with a hand of the operator.

The inlet 120 may be provided in each of two or more first grooves H1. The inlet 120 may include a filter 121 exposed to the outside and a guide member 122 having a hole through which air passing through the filter 121 flows to the gas detector 140.

The filter 121 may filter impurities such as dust, and a plurality of holes may be formed in the filter 121 so that only particles having a predetermined size pass through the filter 121. The guide member 122 is disposed to support a lower portion of the filter 121 so that a fluid smoothly flows to the gas detector 140 inside the case 110.

The power button 130 may press the power switch 180 inside the case 110 to turn the power source on, and when the power button 130 is pressed again, the power switch 180 may return to its original state so that the power source is turned off. The gas detector 140 detects gases contained in air introduced through the inlet 120. The gas detector 140 may include sensors and means for analyzing types, concentrations, and components of gases, and thus harmful gases can be detected. The gas detector 140 may transmit a gas detection signal to the light unit 150, the beep generator 170, and the like only when detecting the harmful gases.

The light unit 150 may be provided in each of two or more of the third grooves H3 and may inform the outside of one or more states in which the power source is turned on or off and whether a gas is detected. For example, in the state in which the power source is turned on, the light unit 150 may inform the state by emitting light emitting diode (LED) light. In addition, when a gas detection signal is received from the gas detector 140, the light unit 150 can visually inform the outside of light repeatedly blinking at regular time intervals. The inlet 120, the power button 130, and the light unit 150 may be provided in circular shapes and coupled to the first groove H1, the second groove H2, and the third groove H3 in a recessed form.

The battery 160 supplies electricity when the power button 130 is pressed. For example, the battery 160 may supply electricity to one or more of the gas detector 140, the light unit 150, and the beep generator 170.

When receiving a gas detection signal from the gas detector 140, the beep generator 170 may generate a beep to audibly inform the outside of the beep.

Meanwhile, when the gas detection device 100 is thrown into a closed space, it is preferable that a surface of the case 110, on which the inlet 120 is installed, face upward.

To this end, the battery 160, which is relatively heavy compared to other means, may be disposed at a lower side in an inner portion of the case 110, a support frame 112 may be provided on the battery 160, and the gas detector 140, the beep generator 170, and the power switch 180 may be coupled to an upper portion of the support frame 112 so that a center of gravity is present at a lower portion of the case 110.

Specifically, the cylindrical battery 160 may be disposed horizontally under the support frame 112, and a seating groove or protrusion (not shown) may be provided in the lower case 110b so that the battery 160 is stably disposed.

The support frame 112 may be formed as a circular flat plate matching an inner diameter of the spherical case 110 and disposed on the battery 15, and protrusions may be provided at two sides so that two ends of the battery 15 are hooked on a lower surface. In addition, installation lines may be drawn on an upper end of the support frame 112 to correspond to sizes and shapes of the cylindrical gas detector 140, the beep generator 170, and the power switch 180 so that the cylindrical gas detector 140, the beep generator 170, and the power switch 180 are disposed at designated positions. In addition, a coupling frame 113 and other auxiliary means which are relatively light may be provided above the gas detector 140, the beep generator 170, and the power switch 180.

A coupling protrusion 113a may be formed at a lower center of the coupling frame 113, and the coupling frame 113 may be coupled to a coupling groove 170a formed in an upper portion of the beep generator 170.

The gas detection device 100 of the present invention may include a transmitter 190 through which information on a harmful gas detected by the gas detector 140 is transmitted to a smartphone 200. An installation position of the transmitter 190 may be variously changed.

The operator may install an application, which may perform data transmission and reception between the gas detection device 100 and the smartphone 200, in the smartphone 200, pairing is performed between the smartphone 200 and the gas detection device 100, and then the gas detection device 100 may be thrown into a place in which gas detection is required.

The gas detection device 100 may transmit information on gas components, types, concentrations, and the like contained in air to the smartphone 200 in real time, and the operator may check the information through a screen of the smartphone 200.

In addition, in another example, powering on or off of the gas detection device 100, the light unit 150, the beep generator 170, and the like may be controlled through the smartphone 200.

The gas detection device 100 may operate in a 1:N manner with two or more smartphones 200.

In addition, when two or more gas detection devices 100 are thrown, the gas detection devices 100 may also transmit detected information to the smartphone 200 through a well-known relay communication method or mesh communication method.

One or more of the gas detection devices 100 can be conveniently carried, can be easily thrown into a place in which gas detection is required, can detect a gas in real time, and transmit information to an external device when the power source is simply turned on, and thus the gas detection device 100 is highly cost effective.

In addition, the gas detection device 100 can prevent mortality accidents by generating LED light and a beep to call attention.

The specific embodiments have been illustrated and described above. However, the present disclosure is not limited in the above-described embodiments and may be variously changed without limitation by those skilled in the art without departing from the gist of the technical sprit described in the appended claims.

The invention claimed is:

1. A gas detection device comprising:
a case in which a plurality of grooves are formed in a circumferential surface;
an inlet which is coupled to a first groove among the grooves and through which air is introduced into the case;
a power button which is coupled to a second groove among the grooves and turns a power source on or off;
a gas detector which is provided in the case and detects a gas contained in the introduced air;
a light unit which is coupled to a third groove among the grooves and emits light to inform an outside of one or more states in which the power source is turned on or off and whether the gas is detected;
a battery which supplies power;
a beep generator which generates a beep when a gas detection signal is received from the gas detector; and
a power switch operated by the power button to turn on or off so as to supply the power from the battery,
wherein of the inlet, the power button, and the light unit are coupled to the grooves in a recessed form,
the battery, the beep generator, and the power switch are provided inside the case, and
the case is formed in a small spherical shape which is carried in a palm of an operator and moved by the operator.

2. The gas detection device of claim 1, wherein:
the case has a shape in which an upper case having a hemispherical shape and a lower case having a hemispherical shape are coupled; and
an outer cover of the case is formed of an elastic material and formed in a shape in which hexagonal shapes are consecutively arranged.

3. The gas detection device of claim 1, wherein the inlet includes:
a filter exposed to the outside; and
a guide member in which a hole is formed so that air passing through the filter flows to the gas detector.

4. The gas detection device of claim 1, further comprising a support frame provided above the battery,
wherein the battery, the support frame, and the gas detector coupled to an upper portion of the support frame, the beep generator, and the power switch are sequentially disposed in the case from a lower side so that a center of gravity is present at a lower portion.

5. The gas detection device of claim 1, further comprising a transmitter through which information on the detected gas is transmitted to a smartphone.

* * * * *